(12) United States Patent
Bowen

(10) Patent No.: US 8,217,900 B1
(45) Date of Patent: Jul. 10, 2012

(54) LIGHT BEAM OPERATED PERIPHERAL DATA INPUT DEVICE FOR USE IN AND OUT OF SUNLIGHT

(76) Inventor: James Harrison Bowen, Elizabeth City, NC (US)

( * ) Notice: Subject to any disclaimer, the term of this patent is extended or adjusted under 35 U.S.C. 154(b) by 343 days.

(21) Appl. No.: 12/617,003

(22) Filed: Nov. 12, 2009

(51) Int. Cl.
*G06F 3/01* (2006.01)
(52) U.S. Cl. .......................................... 345/168; 345/175
(58) Field of Classification Search .................. None
See application file for complete search history.

(56) References Cited

U.S. PATENT DOCUMENTS

| | | | |
|---|---|---|---|
| 4,713,535 A | 12/1987 | Rhoades | |
| 5,378,069 A | 1/1995 | Bowen | |
| 5,469,193 A * | 11/1995 | Giobbi et al. | 345/158 |
| 6,097,373 A | 8/2000 | Jakobs | |
| 6,152,563 A | 11/2000 | Hutchinson et al. | |
| 6,770,864 B2 | 8/2004 | Yan | 345/158 |
| 2009/0027335 A1 * | 1/2009 | Ye | 345/158 |

* cited by examiner

*Primary Examiner* — Wayne Young
*Assistant Examiner* — Brian Butcher
(74) *Attorney, Agent, or Firm* — Whitham Curtis Christofferson & Cook, PC

(57) ABSTRACT

The invention is a light operated peripheral standalone input device to be used in and out of sunlight where input is made by a light beam to the peripheral or other input device where the light beam is pointed at a position from distances near and to over a mile away and the function of that position is input. The invention allows for keyboard input and directional control and cursor positioning to dedicated board level microprocessor driven control systems, personal computers, wheelchair operation, control panels for operating equipment and for those who cannot use their arms and hands for normal computer input like partial quadriplegics or other disabled persons, and persons that need a non-contact input device that is operated from a distance in hazardous areas or underwater with a light beam.

20 Claims, 10 Drawing Sheets

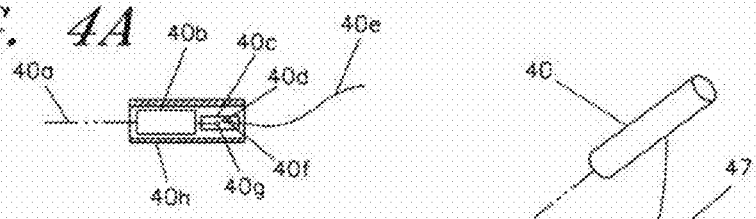
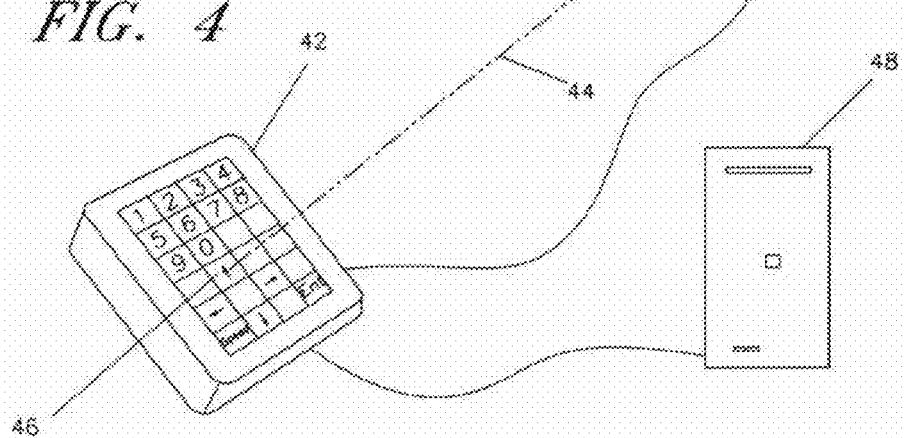
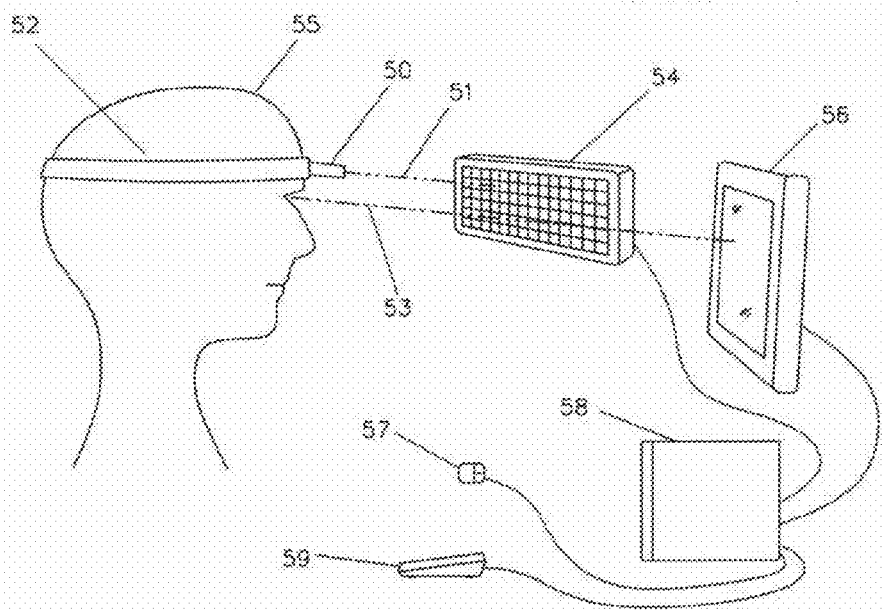

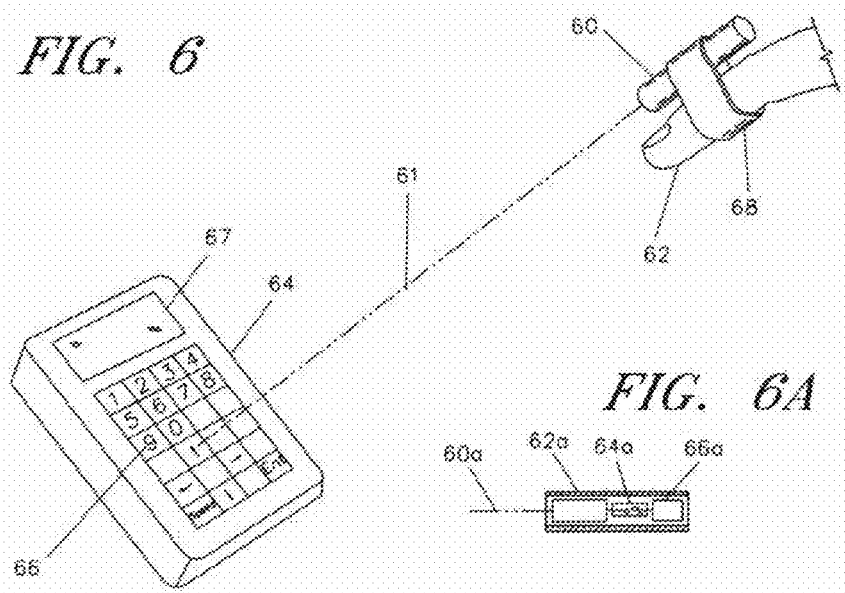
FIG. 6
FIG. 6A
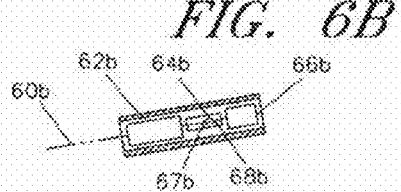
FIG. 6B
FIG. 7
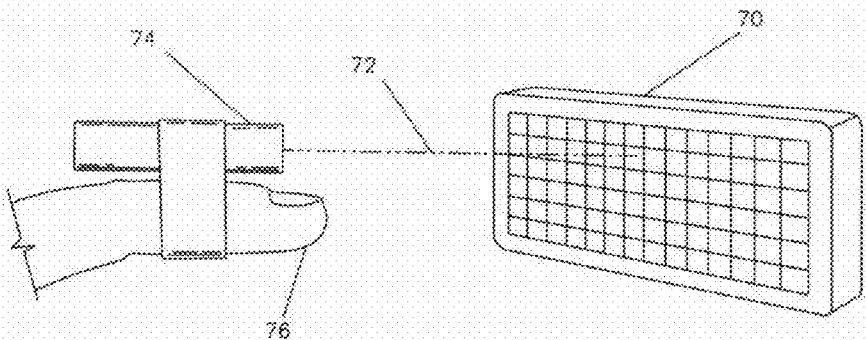

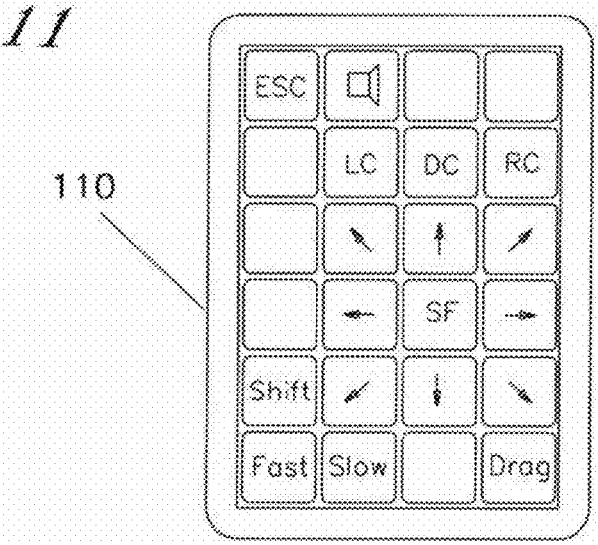
FIG. 11
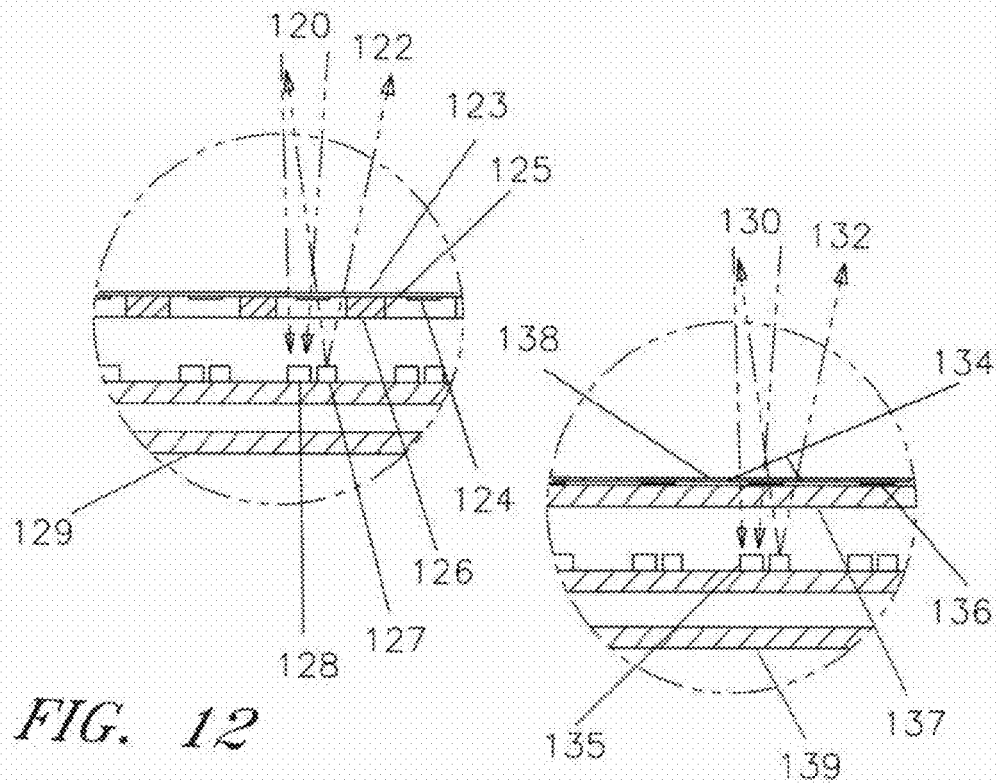
FIG. 12
FIG. 13

LIGHT BEAM OPERATED PERIPHERAL DATA INPUT DEVICE FOR USE IN AND OUT OF SUNLIGHT

BACKGROUND OF THE INVENTION

1. Field of the Invention

The present invention generally relates to a input devices operated from a light beam with automatic ambient light compensation to allow use outside in direct sunlight and inside with varying light conditions, or underwater for keyboard input, directional input and cursor positioning to input to dedicated board level microprocessor driven control systems, personal computers (PC), control panels for operating equipment, control panels for partial quadriplegics to operate a wheelchair and computers, and for other non-contact computer input devices where a light beam is pointed at a position and the function of that position is output to a host, e.g. keyboard characters, data related to symbols, and arrows related to directional input.

2. Description of the Prior Art

Touch screens with a virtual keyboard input into computers have been used for many years. Some have a limited number of keys and some have a virtual qwerty keyboard displayed but needs an operator that can move their arms and fingers to touch the screen, it lacks portability, must use the computers display and processing power, and in it's present form cannot be anticipated mounted to an arm of a wheelchair or used underwater where a user cannot touch the device for input.

U.S. Pat. No. 4,713,533 Rhoades shows a keyboard operated by a light beam either on a table or mounted to a wheelchair with a manual potentiometer that adjusts one fixed threshold reference for all light detectors.

U.S. Pat. No. 6,097,373 Jakobs shows a keyboard operated by a light beam for desktop use that uses a frequency emitted light beam to filter out background electronic noise.

U.S. Pat. No. 6,770,864 Yan shows an optical input apparatus that uses a specific photodiode to validate other photodiodes.

U.S. Pat. No. 6,152,563 Hutchinson shows an eye invasive light activated virtual keyboard displayed on a computer monitor where a light beam, is received into the eye and then reflected to a monitor to select keys on the displayed virtual keyboard. This beam cannot be projected from a distance so the beam from emittance to monitor detection must be in very close proximity to the monitor emitting the beam. The apparatus needs separate optics hardware, lacks portability, needs to be in close proximity to computer and computer monitor, the price is high, needs to use the host computer for processing power, and in it's present form cannot be anticipated or obvious how such a device of this size would be mounted to an arm of a wheelchair, used underwater, or outside in direct sunlight.

U.S. Pat. No. 4,602,907 Foster and U.S. Pat. No. 6,061,052 Raviv et al shows a monitor as an output device emitting a beam being monitored by a photo sensor in a pen like device that must be in very close proximity to the monitor emitting the beam, and then through the computers processing power determines where the monitor output is detected, and in it's present form cannot be anticipated or obvious how such a device of this size would be mounted to an arm of a wheelchair or used underwater, or outside in direct sunlight.

U.S. Pat. Nos. 5,378,069, 5,577,848, 5,605,406, 5,707,160, 5,785,439, Bowen show a keyboard that detects an operators finger optically.

Another technology to aid partial quadriplegics in using a computer is very simple in concept but is being used are mouth sticks to depress keys on a keyboard, and head sticks to depress keys on a keyboard and to control wheelchairs. Where a stick is placed in a person's mouth or attached to the head and by using head movement the stick is positioned on an input position.

Still another technology to aid partial quadriplegics in using a computer is a head tracking software and hardware device that watches changes in head movement to position a cursor on a monitor.

Still another technology to aid partial quadriplegics in using a computer is voice recognition but has limits to being portable in as much as to be effective it has to be thought to a user's pronunciation making it computer specific.

SUMMARY OF THE INVENTION

The invention being an input device or control panel that is solid state with no moving parts and actuated by a light beam for use by quadriplegics, either outside in direct sunlight or inside in varying light conditions using automatic ambient light compensation, either battery powered or connected to a power source, allowing physically challenged persons to use a computer or host, and in other applications by using a light beam it can be a non-contact input device or control panel for control of wheelchair, machines and other apparatuses, and having the sunlight rejection means in the input device so a battery powered unattached light source can be used.

It is therefor the primary objective of this invention to have an input device with character and cursor input that is light beam operated. The characters can be but not limited to a full qwerty pattern or a minimal pattern of just a few key locations. Quadriplegics do not have proper motor skills to operate regular keyboards and mice. Quadriplegics who can move a finger, head or toe, or other part of their body can have a light beam attached to the moveable part of their body and direct it at the device to input characters or control cursor movement.

A further object of the invention is to be able to be small in size facilitating being mounted in small areas used for wheelchair control or other machinery control.

A further object of the invention is do a baseline scan to use as a reference to digitally filter out sunlight or water distortions from the light beam input to facilitate light beam detection, and to repeat the baseline scan as necessary.

A further object of the invention is to be used underwater as a physically non-contact input device.

A further object of the invention is to be used with small board level control systems that do not have monitors, personal computers or main frame computers and need all key scanning and detection within the input device that only output key codes.

A further object of the invention is to be a peripheral input device to a computer and not use the processing power of the host computer in as much as a PC uses a separate integrated circuit to interface with a user interface device that receives key input and then only minimal processing time to route data to a monitor or other running program freeing the computer from doing the key interrogation or detection to decide if and what is being input.

A further object of the invention is to be small and rugged and easy to be transported from hospital room to another hospital room, or hospital to home, or home to someone else's home where the user needs only plug the input device in or through wireless communications having no physical contact to the host and being hands free start using the input device to use the computer.

A further object of the invention is to have complete computer control within one device so persons with reduced motor skills have one input device, one cable that can be plugged into a host, or wireless where no cable is needed. So when a plug is needed the person with limited motor skills using this device will not be able to plug the input device into a host or turn the computer on, so with their limited verbal help and no physical help can instruct someone with limited computer skills like a hospital orderly to just plug the input device into the host or just turn on the host, and without other drivers to be loaded or hardware to be installed can begin to input data to a host.

A further object of the invention is to be low cost.

A further object of the invention is to allow operation of the invention from long distances through windows of control rooms, and through hazardous areas.

A further object of the invention is to be solid state and have no moving parts facilitating long operational life with little maintenance.

A further object of the invention is to output voice commands and enunciate characters from the input device.

A further object of the invention is to have a display to show which input position was detected.

To receive an input and to be able control any apparatus in direct sunlight and allowing the apparatus to move inside out of direct sunlight with automatic compensation is not trivial. The applicant for this invention has ten years experience in designing and manufacturing optical keyboards to be used in sunlight and in offices with seven U.S. Patents on optical keyboards being used in sunlight, and thirty five years in engineering with knowledge beyond those ordinarily skilled in the art to make an optical keyboard operate in varying light conditions. By doing a baseline scan of all of the input detectors to receive the current ambient, the detectors with different gains are stored for reference. When using a plurality of detectors the from detector to detector gain can be two hundred percent different from each detector so in practice a single threshold for all detectors would not be useable and discussed below where in sunlight and out of sunlight can only be a few counts of difference in an analog to digital circuit (A/D) to show detection. By using the A/D circuits within the microprocessor in the input device and dividing the input voltage into one thousand counts and using sense resistor 175 of FIG. 17 to give about one hundred counts to equal inside ambient light and about seven hundred counts when in direct sunlight. If a laser is being used to select a position and the laser intensity when directed at a photo detector will give about seven hundred counts, then multi-sampling summing digital signal processing (NSSDSP) needs to be used to separate the sunlight from the laser. Or said in a basic calculation if you turn the laser on and sample the input and then turn the laser off and sample the input up to four or more times, depending on the application, the sum of the inputs will equal laser detected or not detected, there is no frequency involved the sun just emits a DC offset component. Even more basic if you get a count of seven hundred with laser on in one sample and laser off, equaling ambient, sample of six hundred and night-eight or plus two counts with laser on then after four samples the sum would be eight, which depending on the application, would be enough to equal a detection. In the case where the laser is battery powered giving the user much more freedom of movement then the input device that is updating the baseline scan on a regular bases and storing that baseline scan number for each detector, then instead of comparing the amplitude of the A/D when the laser is on and then off, the laser is compared to the stored baseline scan number resulting in a similar number as controlling the laser on and off.

Using a manual potentiometer to adjust a fixed threshold reference for all of the optical inputs would in practice either saturate the detectors in direct sunlight or be non-responsive out of sunlight or anywhere in between and a person trying to input to a computer would find the computer non-responsive. In the case of using a low frequency modulation of the laser to filter out noise the same saturation problem would occur, the sun does not emit noise just a DC offset component. A person in a wheelchair could be on a street outside and stop for a red light and unaware to the person in the wheelchair position themselves under an over head wire or other obstruction and the input control then being shaded would stop operating without automatic ambient compensation.

After years of testing a florescent light like used in most offices with the proper sense resister it has no effect on IR or other wave length detectors in either amplitude or frequency shift. While incandescent lights simulating the sun give a large DC component on both detectors, but where the sunlight scenario remains is if the person using the input device is in an office and is positioned by or close to a window or near an incandescent light the intensity is very similar to being outside. It is therefore very advantageous for this invention to have an input device or keyboard that is light beam activated that can be used outside in direct sunlight and inside or near and far from a window with sunlight being present.

BRIEF DESCRIPTION OF THE DRAWINGS

The foregoing and other objects, aspects and advantages will be better understood from the following detailed description of the invention with reference to the drawings, in which:

FIG. 4 shows a light source emitting a light beam at a control panel for computer data input or the like with indicia in fixed locations in accordance with the teachings of this invention;

FIG. 4A shows a cutaway view of a light source that is wired to the control panel with a tilt switch for power on/off in accordance with the teachings of this invention;

FIG. 5 shows a light source mounted on a persons head emitting a light beam toward the input device while the eye is watching the resultant input on a monitor in accordance with the teachings of this invention;

FIG. 6 shows a light source mounted on a finger emitting a light beam at a control panel in accordance with the teachings of this invention;

FIG. 6A shows a cutaway view of a light source that is battery powered with a tilt switch for power on/off in accordance with the teachings of this invention;

FIG. 6B shows a cutaway view of a light source in a tilted position that is battery powered with a tilt switch for power on/off in accordance with the teachings of this invention;

FIG. 7 shows a light source mounted on a finger emitting a light beam to operate an input device in accordance with the teachings of this invention;

FIG. 11 shows a key layout of a control panel with characters, symbols and directional arrows in accordance with the teachings of this invention;

FIG. 12 shows an enlarged view of detail "A" from FIG. 5 with an opaque housing with holes through the housing at character locations in accordance with the teachings of this invention;

FIG. 13 shows an enlarged view of detail "A" from FIG. 5 with a transparent or semi-transparent housing in accordance with the teachings of this invention;

DETAILED DESCRIPTION OF THE INVENTION

Figure 1:
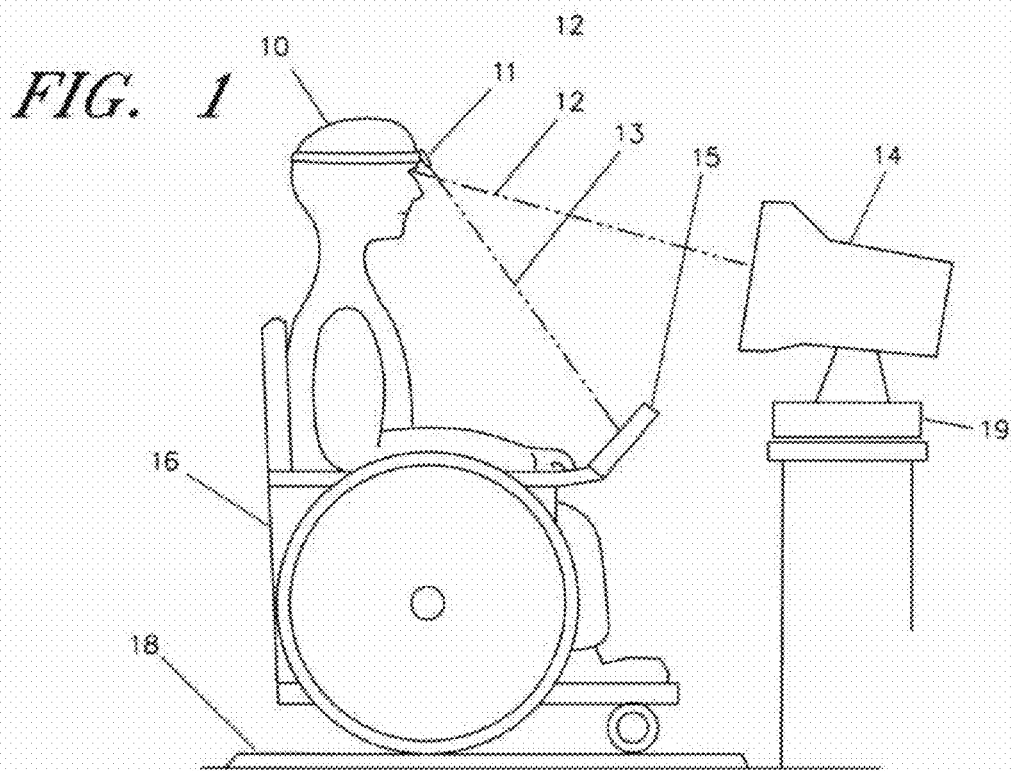
FIG. 1 shows a person in a wheelchair controlling their wheelchair with a light beam directed at the wheelchair controls and then rolls up to a computer station and via a wireless system like blue tooth or sensitive matt and without any physical connection to the computer station is able to operate the computer with the same light beam that controls the wheelchair and operate a light operated keyboard input device for data entry and cursor control in accordance with the teachings of this invention.

Referring now to the drawings, FIG. 1 shows a person 10 in a motorized wheelchair 16 that is controlling motorized wheelchair 16 with a light beam 13 emitted from light source 11 directed at the motorized wheelchair 16 input controls 15 which rolls up to a computer station with computer 19 and monitor 14 and via a wireless system like blue tooth, sensitive matt 13 or other RF technology and without any physical connection to the computer station is able to operate computer 19 with the same light beam 13 that controls the motorized wheelchair 16 and operate input controls 15 that can include wheelchair controls and a light activated keyboard input device with qwerty key pattern for data entry and cursor control to computer 19. When using a wireless connection, the host wireless connection in computer 19 can recognize input controls 15 when in close proximity, or with sensitive matt 18 when motorized wheelchair 16 comes in contact it can signal computer 19 to emit a signal to start communications with input controls 15 to allow operating computer 19 by sending data from input controls 15 to computer 19 and being seen by person 10 on monitor 14 via eye beam 12. Showing that a quadriplegic or other physically challenged person without help can operate a computer unassisted in their home, hospital, mall or anywhere they want to travel. Besides allowing physically challenged persons the ability to access computers via light beam 13 through input controls 15 this is also advantageous to allow the most freedom and self esteem for quadriplegics and other physically challenged person to have a feeling of self independence whether being in a room near or far from a window. Another advantageous feature is light beam 13 does not have to be perpendicular to input controls 15 for data entry allowing physically challenged persons in wheelchairs to operate computer 19 in their most comfortable position. When the physically challenged person is ready to leave they can select the OFF/ON key 100a of FIG. 10 and turn off all or part of input controls 15 like leaving on input controls 15 and turn off the keyboard function.

Figure 2:
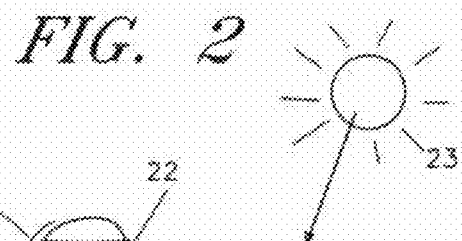
FIG. 2 shows a person in a wheelchair that is controlling their wheelchair with a light beam directed at the wheelchair controls in direct sunlight in accordance with the teachings of this invention.

FIG. 2 shows person 26 in motorized wheelchair 20 controlling their motorized wheelchair 20 with light source 22 emitting light beam 24 directed at wheelchair controls 25 in direct sunlight 23 using slight head movement 21 to direct light beam 24 to select control positions like forward, stop, turn right, and other controls from wheelchair controls 25 communicating with wheelchair computer 28 for actual control of motorized wheelchair 20. Wheelchair computer 28 needs to be as small as possible because of weight and the amount of wheelchair battery life reduced if a typical PC and monitor would be used and transported with motorized wheelchair 20, and size is important also because there is only small amounts of room being very conducive to board level size computers because they are small and just for the purpose of controlling wheelchairs. Wheelchair computer 28 buy using wheelchair controls 25 all of the key scanning is in wheelchair controls 25 enabling wheelchair computer 28 to only have to receive and process key codes again allowing for a smaller board level control system, as opposed to input systems that are based around PC's where all or most of the key scanning detection and interrogation of inputs are using PC computer processing power.

Wheelchair controls 25 although shown being mounted to motorized wheelchair 20 is a standalone device because it can be used unattached from motorized wheelchair 20 and just using a communication cable to connect to a wheelchair computer 28 as in but not limited to training of the controls when a training person would walk alone side a person in a wheelchair and show them the proper use of the controls. Another advantageous feature of having a light beam activated keyboard is if a person trying to help person 26 to move or reposition motorized wheelchair 20 would accidently touch wheelchair controls 25 then nothing would happen as in moving inadvertently and injure someone, where with push buttons on normal wheelchair controls could be pushed and activated.

If person 26 also has a speech impediment wheelchair controls 25 can by selecting a position on wheelchair controls 25 with light beam 24 emit a help phrase or other command to be heard by a person in close proximity for help or service person 26 might need.

Figure 3:
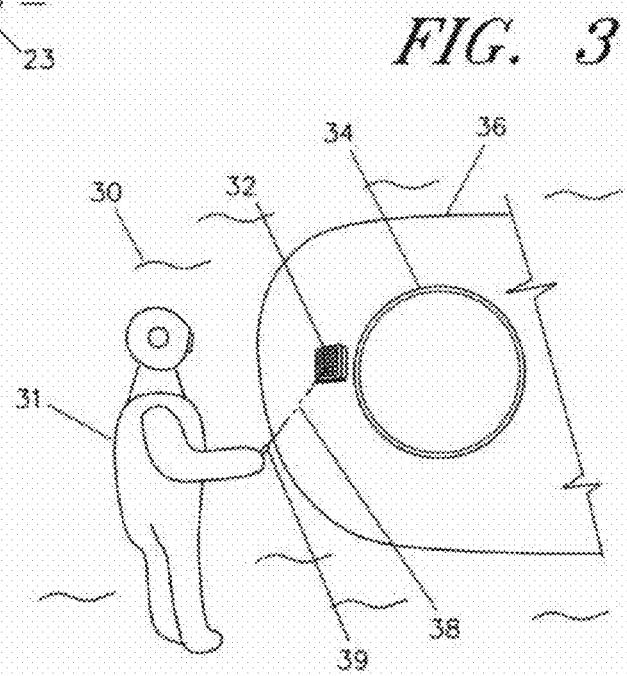
FIG. 3 shows an underwater diver accessing a diving chamber with a light beam directed at a control panel to open the sealed hatch in accordance with the teachings of this invention.

FIG. 3 shows diver 31 in deep water 30 holding light source 39 emitting light beam 38 accessing diving chamber 36 via input device 32 through using codes input device 32 are transmitting to a host to open the sealed hatch 34. This is advantageous because input device 32 has no moving parts and no moving keys making input device 32 easy to seal and with no moving parts long lasting and low in cost, and with input device 32 having automatic light compensation light source 39 can be used in varying water clarity.

FIG. 4 shows light source 40 emitting light beam 44 onto control panel 42 at one of the twenty locations of control panel indicia 46 and holding light beam 44 for a period of time an output associated with key indicia 46 is sent to computer 48. Key indicia 46 is fixed in position because indicia 46 is disposed on a surface and is not displayed on a CRT or other monitor output device where characters are changing in location to suit a particular application requiring addition cost, size and weight, and cannot be easily sealed, and if sealed the watts necessary to operate a monitor reduce battery life. This is advantages for a physically challenged person because once the person learns key indicia 46 pattern then it will always be the same. Light source 40 is shown connected to control panel 42 for power and can then be controlled as to on and off periods for saving power and LED life, or can be battery powered if a user does not what to have a tethered light source. Control panel 42 is connected to computer 48 for bidirectional data transfer to control computer 48. The data from control panel 42 can be key inputs the same as regular keyboard inputs and cursor directional input the same as a regular mouse would input for computer control. Light beam 44 does not have to be in a particular alignment, as long as a user sees light beam 44 over the key indicia 46 and the position emitter lights up then that key is selected, so perpendicular alignment and central axis is not necessary to select a character. Even distance from light beam 44 to control panel 52 is not important. Key indicia 46 can be made larger so input could be from across a room or through a window, this can be especially advantageous when working around hazardous areas because control panel 52 could be in a hazardous area and a user could be in a non-hazardous area operating control panel 42 through a window. And the only constraining factor in distance is how big the key indicia 46 is, and if you are using a telescope and light source 40 is a laser then control panel 42 could be used over a mile away.

FIG. 4A shows a cutaway view of a light source 40h with light diode circuit 40b emitting light beam 40a with tilt switch 40c and contact 40g and contact 40f with mercury 40d that is powered via wire 40e. Tilt switch 40c is shown in the off position and if tilt switch 40c is rotated mercury 40d would move over and connect contact 40g and 40f, it should be appreciated to those skilled in the art how mercury tilt switches work and also appreciated that other types of proximity switches or even motion switches could be used to show head movement and angles.

FIG. 5 shows a light source 50 mounted on a persons head 55 via head band 52 emitting light beam 51 toward input device 54 showing a matrix of key indicia positions and by selecting a key indicia position the eye via eye beam 53 is watching the resultant input on monitor 56 via the connection to computer 58.

Input device 54 being a standalone device similar to a desktop keyboard is connected to computer 58 for bidirectional data transfer to control computer 58. Input device 54 can be mounted on a stand or put in an appropriate position to be seen for easy selection of key indicia by a user. When persons head 55 is moved light beam 51 is seen moving over the surface of input device 54 to select a position showing which data to input. It should be appreciated by those skilled in the art that laser light sources at first glance would be a first choice but light pipes and other directional light beams could be used. Mouse 57 and keyboard 59 are shown also connected to computer 58 but are not necessary unless a user desires.

FIG. 6 shows light source 60 that is battery powered and not connected to control panel 64 mounted on finger 62 emitting a light beam 61 at a control panel 64 with indicia 66. Those skilled in the art can appreciate that the shown twenty positions on control panel 64 could be more or less depending on the application for control panel 64 as in the showing in FIG. 7 control panel 70 that has for example eighty-four positions. Light source 60 as shown is attached to a user's finger 62 by Velcro 68 but those skilled in the art appreciate that other means of attachment could be used such as molding made to fit a finger other attachment devices as in FIG. 5 head band 52. Also those skilled in the art can appreciate that the light source can be held and not attached to an appendage of the body depending on motor skills of the user, or even held in the mouth of the user. One must appreciate that partial quadriplegics are different in as much as which part of the body can be moved, even light source 60 could be mounted on a user's toe to be positioned over indicia 66 of control panel 64. The distance from light source 60 to control panel 64 is not important or is the optical alignment because all that is necessary is for the user to see light beam 61, so finger 62 could be touching control panel 64 and light source 60 could be less than an inch away or across the room just depending on how large indicia 66 is so it can be seen by the user.

When this invention is used in other applications light source 60 can be held by a person at a distance from the control panel only limited by the size of the indicia so visual recognition can be made for selecting the correct function of control panel 64. In hazardous areas whether the user is in the hazardous area and control panel 64 is operated through a window, or control panel 64 is in the hazardous area and the user positions light source 60 through a window or other protective transparent shield the user can be isolated when operating control panel 64. Most light sources are diffused by water but when used in a close proximity light source 60 can select indicia on control panel 64 through water making an isolated and sealed underwater control panel. In some applications display 67 can be used to show which key is detected. Depending on the application the key shown can be displayed or the option to have a word as indicia then just one key code can be sent, like the indicia could say print, and the letter p could be displayed. The application might need key codes to be sent only to display 67 and not to the host until a send key would be detected then the string of key codes would be sent to the host. In bi-directional communications the host could send a prompt to control panel 64 requesting a response from a user operating at control panel 64.

FIG. 6A shows a cutaway view of light source 62a being powered by battery 66a emitting light beam 60a with tilt switch 64a in the off position when not pointed in a downward direction.

FIG. 6B shows a cutaway view of light source 62b being tilted in a downward direction allowing mercury 64b to connect forward connector 67b and rearward connector 68b to connect power from battery 66b to light source 62b. This is advantageous to disconnect light power when a user directs light source 62b in an other than a downward direction. It should be appreciated that those skilled in the art could adjust the angle of light source 62b to be on an off in varying degrees depending on the application. So normally when a person is using a computer and looking down light source 62b is on and powered and when as in FIG. 6A light source 62a is not pointing down light source 62a is turned off. This is a safety issue if a laser is being used in light source 62a and not being used in a computer cubical to not allow the user to look up and around that might allow the laser beam to be directed at other persons. The tilt switch feature is also advantageous to save battery life and being battery powered it frees the user from being attached to an input device or keyboard. It should be appreciated that the tilt switch can be used in any of the light sources in this preferred embodiment.

FIG. 7 shows light source 74 mounted on finger 76 emitting light beam 72 toward input device 70 showing that any number of input positions can be selected by light source 74.

Figure 8:
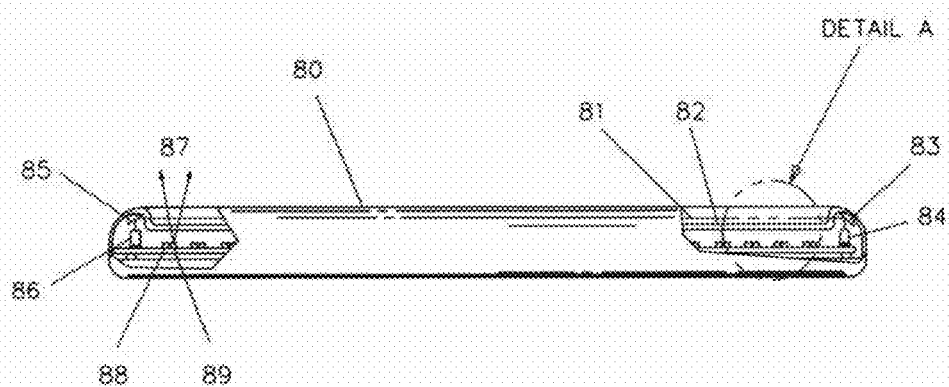
FIG. 8 is a side view of an input device showing finger detection and photo sensors and LED's in accordance with the teachings of this invention.

FIG. 8 is a side view with internal partial views of input device 80 showing finger detection photo sensor 86 emitting a finger detection beam 81 that is reflected off of photo sensor mirror 85 from LED mirror 83 from finger detection LED 84. When a finger blocks finger detection beam 81 the key location at that point is communicated to a host. Key position photo sensor 88 detects a light source and key position LED 89 emits key detection beam 87 responsive to key position photo sensor 88 detecting a light beam. Input device 80 can be used when a user wants to finger input data to a computer, and be able to input data to a computer using a light source. When finger input is needed top surface 82 is in a unilocular area as shown, when finger detection is not needed top surface 82 is a planar surface as shown in FIG. 6.

Figure 9:
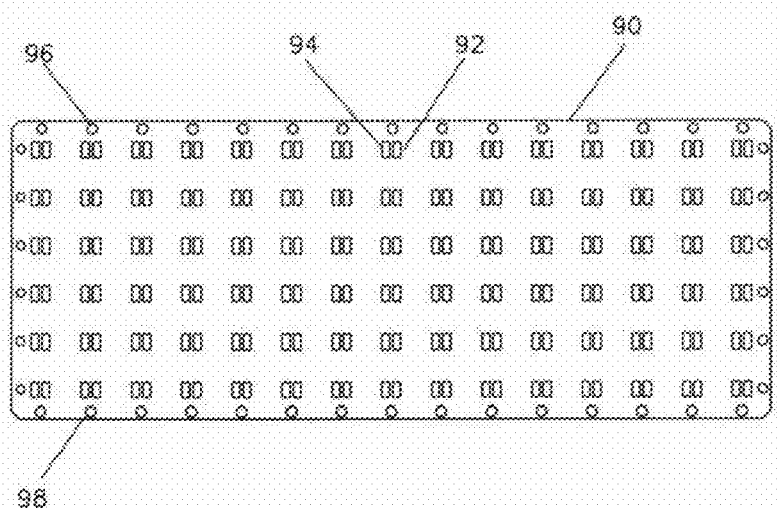
FIG. 9 shows a printed wiring board with photo sensors and LED's mounted next to each other at each of the input locations in accordance with the teachings of this invention.

FIG. 9 shows printed wiring board 90 with a plurality of photo sensors where photo sensor 94 is but one, and a plurality of LED's where LED 92 is but one mounted next to each other defining a plurality of input pairs. Whatever the indicia pattern is as shown in the example in FIG. 4 on control panel 42 and in FIG. 10 control panel 100 there is an input pair behind each one of the indicia positions. In some applications LED 92 is not needed if the user does not need the acknowledgement that an indicia position has been selected. Around the periphery of printed wiring board 90 there are a plurality of finger detection photo sensors 96 opposed by a plurality of finger detection LED's 98 forming a X-Y matrix so when a finger is placed in the matrix the X and Y position is recorded and the function where the finger is placed is input to a host.

Figure 10:
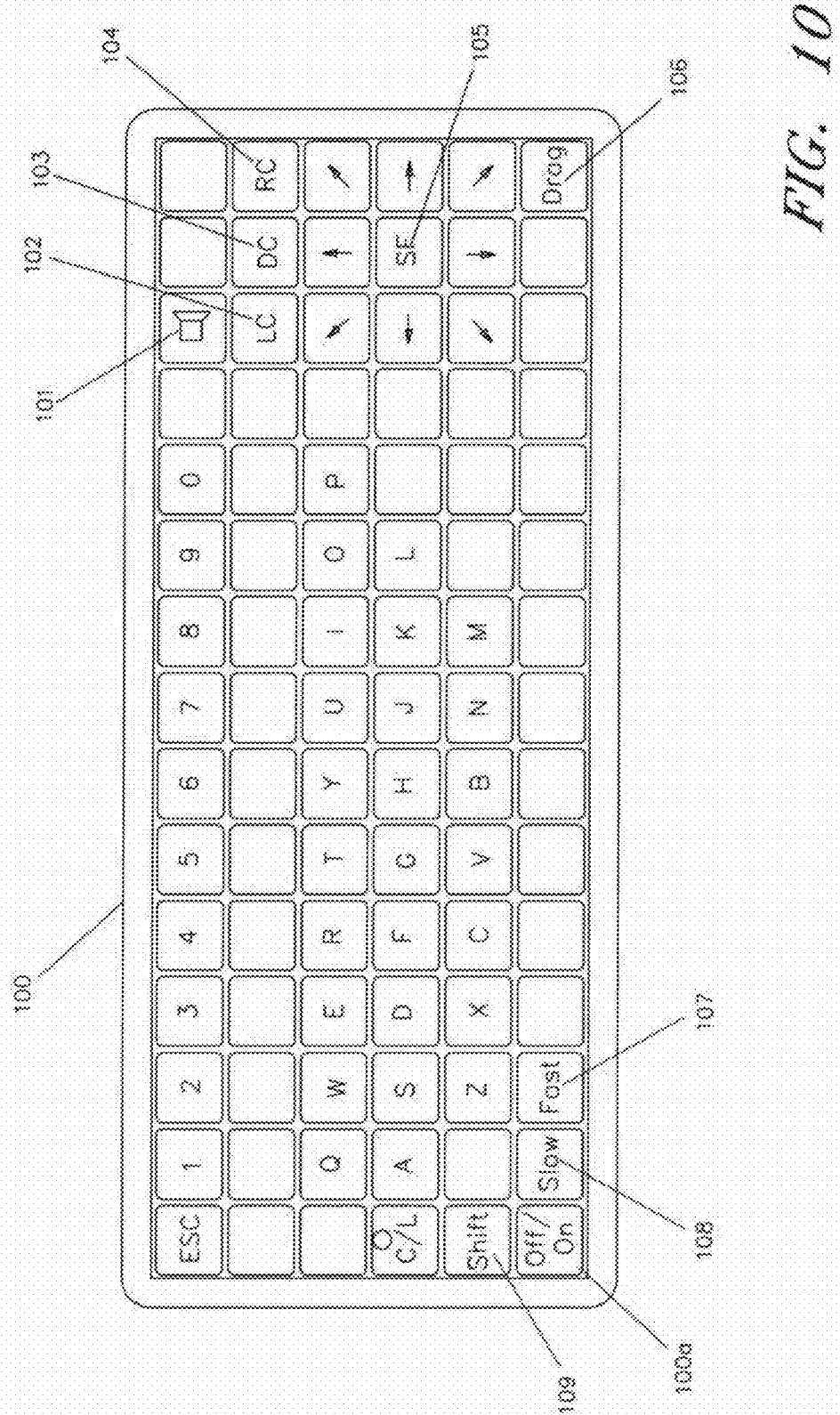
FIG. 10 shows a key layout of an input device with characters and cursor positioning functions in accordance with the teachings of this invention.

FIG. 10 shows a key layout of input device 100 with characters and cursor positioning functions. Those skilled in the art will appreciate that this key layout and function could be changed to fit other applications with more or less keys and any number of different symbols sending any number of different outputs or macros. This layout shows that input device 100 in one unit, using one technology, including a keyboard and mouse allowing control of a PC or other apparatus, which is very advantageous when a person is physically challenged only needs to have one apparatus to carry. This key layout shows speaker key 101 that allows the user to increase or decrease the audio feedback speaker in which it can be a beep or voice commands where they can be heard by the user or a help person, or it can turn the audio feedback or voice commands off and on. The speaker can also be on an umbilical cable to be placed in the users ear so each key can be enunciated to help in outputting the correct key to the host. Speaker key 101 is operated like all of the keys on input device 100 by which placing a light beam on the key the light, beam is detected and the function is input, either to the PC or to only input device 100, or to both. When using the X-Y matrix finger detection as shown in FIG. 8 and FIG. 9 by touching speaker key 101 the finger is detected by the X position and the Y position and gives the same function as using a light beam. FIG. 10 shows LC key 102 when light is detected inputs the left click function of a standard computer mouse. DC key 103 when light is detected inputs a double left click function of a standard computer mouse where the timing interval is fixed by input device 100 and not by the user for ease of operation for those with limited motor skills. RC key 104 when light is detected inputs the right click function of a standard computer mouse. When the shown arrow keys detect a light beam a cursor is moved in position first starting slow for finer selection on a monitor display then the movement speed increases to facilitating rapid traverse across a monitor. SF key 105 is the start fast key and if a user wants to move quickly first to rapid traverse across the monitor display the user can first touch SF key 105, then an arrow key and the cursor will move quickly at first, then when the user removes the light beam from the arrow key and then positions the light beam again over the arrow key it will again start slow.

To move an object or icon on a monitor display one of shown arrow keys positions the cursor over an object then Drag key 106 detects a light beam and a left click is sent and appropriate other signal by Drag key 106 to enable moving the object, then one of arrow keys detects a light beam and the object is moved in the direction of the arrow, then when the arrow key does not detect the light beam the object stops in position and the signals started when Drag Key 106 started are reset and input device 100 awaits further detection. Fast key 107 is used to decrease the detection time of a key position by decrementing the delay timer to a smaller time to speed up detection. Slow key 108 is used to increase the detection time of a key position by incrementing the delay timer to a larger time to slow detection.

This is very advantageous because as an operator gets more familiar with the use of input device 100 the operator can increase the speed of response to increase the PC input times, and when used by multiple operators the next operator can then slow down the response for their skill level without having a technician do an adjustment for them. When shift key 109 detects a light beam the next key detected is shifted to the second function on a key, if a letter key is selected then the letter is shifted to upper case and then Shift key 109 is reset to allow lower case or normal characters to be sent.

Input device 100 can be controlled by a host it is connected to, when num-lock or scroll-lock function are not used on input device 100 since these codes are sent from the host to input device 100 they can be detected and used for different functions, but not limited to, turning input device 100 on and off, or prompting the user to perform a function. OFF/ON key 100a can be used to turn on or off different functions of input device 100, and then if off can be turned back on by host emitting a command like S/L or other command depending on the application.

FIG. 11 shows a key layout of control panel 110 with characters, symbols and directional arrows with same type of function as FIG. 10 input device 100 except with a more limited character and function set, and showing any number of key positions more or less can be used as needed by other applications like control of a wheelchair.

FIG. 12 shows an enlarged view of detail "A" of FIG. 8 showing an optional opaque housing 126 with key position through holes 125 and indicia 124. Graphic overlay 123 is used to display print, mold or inscribe indicia 124 at each key location or detection point. Using a textured material for graphic overlay 123 is optional but with some light sources texturing stops the reflection back at the user or in various direction. By using opaque material for the housing the material is cheaper and covers up the internal components without further finishing of the housing like painting or covers. Further graphic overlay 123 seals key position holes 125 from outside contaminations getting into input device components, this assures that if any fluids are present they are sealed from the internal parts that opaque housing 126 and lower housing 129 encompass. Light beam 120 is detected by light detector 98 and then LED 127 is illuminated. A delay that can be adjusted by Slow key 108 and Fast key 107 of FIG. 10 is then started and a verbal enunciation of which key has the delay started so if the user has selected the wrong key the light source can be moved to another position, if the user moves light beam 120 to another position during the delay the delay is reset and no output to the host is made, if the delay times out and light beam 120 is still over that position then the output of that position is output to the computer or host, or in the instance a position of a function key position then the input device acts on the function and may or may not be output to a host computer. In some applications the delay can be fixed to a specific time, and when a user gets the input device the delay or selection time is set or fixed to a mean delay. The delay from detecting light beam 120 until outputting data is so when a person is learning the input device they can have plenty of time to have light beam 120 search over the key positions to find the correct key and then input it without getting false outputs. Then when the user gets more proficient they can speed up the selection time to make faster outputs.

Light beam 120 can be a focused beam from a LED or for longer distances a laser LED can be used. Depending on cost light detector 128 can either be in the infrared region which are cheaper or in a visual region which are more expensive. Light beam 120 needs to be seen on graphics overlay 123 by the user so if an infrared photo sensor is used it would need to have a wave length in the area of about 780, or higher if a dual diode laser is used with an infrared and visual diode. Colors for the visual light beam can be any color depending on the user and the application. It should be appreciated by those skilled in the art that the matching of wave lengths with light beams and light detectors is a cost verses performance issue with maybe using two lasers or one laser with dual emitters one in the visible range for seeing the spot and one in the IR range for using the low cost light detector focused at a user desired distance might very well be the best option.

FIG. 13 shows an enlarged view of detail "A" from FIG. 8 optionally using a transparent or semi-transparent housing 137 allowing for light beam 130 and LED beam 132 to pass through housing 137. Depending on the application graphic overlay 138 can have opaque coloring 134 to show the outline of indicia 136 over the corresponding key position similar to a key position through holes 125 of FIG. 8. With transparent housing 137 there is no need to have graphic overlay 138 to seal the input device, because the enclosure formed by housing 137 and rear cover 139 can be sealed to protect the internal parts. And using housing 137 the indicia and key position locational graphics can be screened directly on housing 137, or molded into housing 137. It should be appreciated by those skilled in the art that there are other ways to mark a housing and molded and screened are but two.

The distance from the light source emitting light beam 130 to light detector 135 is not important, and when using a hand held battery powered laser it can be over a mile away, or is the optical alignment because all that is necessary is for the user to see light beam 130 over the key indicia, this is because of the close proximity from indicia 136 and the beam divergence from the textured material of graphic overlay 138, or if there is no graphic overlay 138 and the indicia is disposed on transparent housing 137 and divergence from housing 137 effecting light beam 130. It should be appreciated that those skilled in the art that housings 137 could be different degrees of transparency from semi-transparent to transparent and in various transparent colors and also textured in various degrees.

Figure 14:
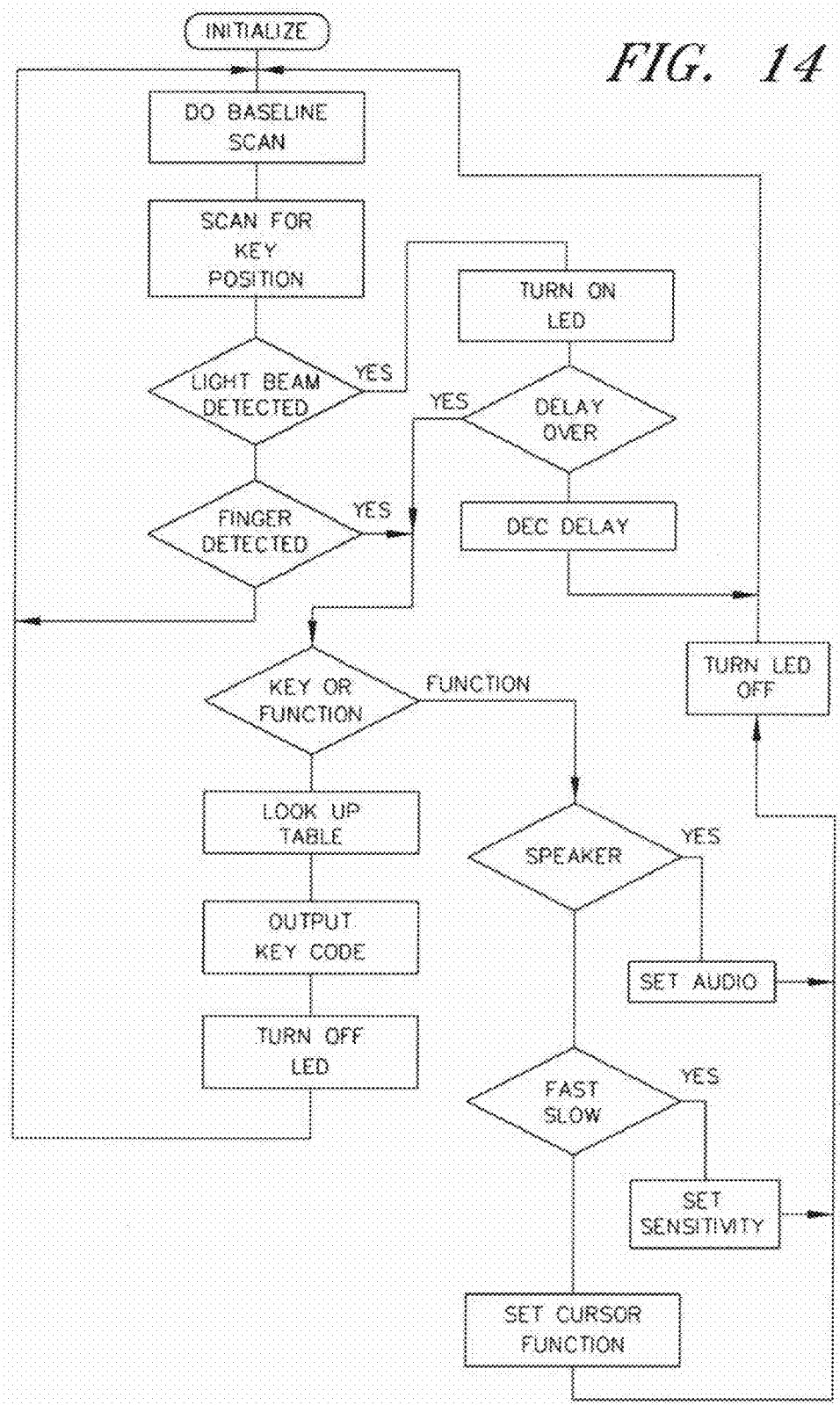
FIG. 14 is a flow chart showing the program in the microprocessor for controlling the input device in accordance with the teachings of this invention.

FIG. 14 is a flow chart showing the program in the microprocessor for controlling the input device or control panel.

It should be appreciated that those skilled in the art could use more than one microprocessor or other processor type integrated circuits like PLA's in combination with or without a microprocessor and that using a microprocessor in this preferred embodiment would include any processing means within the input device. In INITIALIZE power is stabilizing, RAM is being checked, ports are being set for input, output and analog functions. In DO BASELINE SCAN a check is made if any baseline values have been stored, the first time through there would be no values, if there are no values then a baseline scan is done by scanning indicia position photo sensors and the value is stored to be used to compare an ambient measurement of brightness so a difference between a light beam and ambient light can be calculated. If values have been stored then a few photo sensors can be scanned to check if the ambient has changed as in if the ambient has changed from a dimly lit room to a direct sunlight ambient, if a difference is detected then a complete baseline scan is done and new values are stored. If ambient lighting in areas are not such that a baseline scan is needed to be repeated the baseline scan could only be done at start. A configuration register in the processing means can be used for these selections that is programmed when the processing means is programmed, one bit in the register could be for, do only baseline scan at startup, another bit could be, only scan a few detectors to check current ambient. At SCAN FOR KEY POSITION the program through scanning the light detectors is looking for a difference from the baseline stored ambient value to detect a light beam or finger using multi-sampling summing digital signal processing as heretofore mentioned to achieve automatic compensation for different light conditions, and as the application may require one or more multi-samples could be used, here again the configuration register can be used to say one sample or more samples depending on the application. When a difference is detected the program checks to see if it is a light beam at LIGHT BEAM DETECTED or a finger at FINGER DETECTED and if neither saying it was a false record then the program goes back to DO BASELINE SCAN to scan again. If at LIGHT BEAM DETECTED it is a light beam then the LED at that position is turned on at TURN ON LED and a delay is started to make sure that the user wants to select that position or is just passing over that position so if a length of time is sufficient it is tested at DELAY OVER, if not over then the program returns to DO BASELINE SCAN to continue scanning again, if the delay is over the program goes to check if it is an output key or function. If a key position is detected the program goes to LOOK UP TABLE to convert the key position to an output code, the key code is output at OUTPUT KEY CODE to the host computer, then to turn off the LED at TURN OFF LED and returns for a new scan at DO BASELINE SCAN. If a function is detected at KEY OR FUNCTION then a test to see if it is for adjusting the speaker output amplitude at SPEAKER if YES the audio is set at SET AUDIO then the position LED is turned off at TURN LED OFF and return for a new scan at DO BASELINE SCAN. If the speaker function code is not detected at SPEAKER then the codes to set the delay from LED on to LED off is checked at FAST SLOW if the fast slow led codes are detected then the delay is changed to the new code at SET SENSITIVITY, then the led is turned off at TURN LED OFF and return for a new scan at DO BASELINE SCAN. If the fast slow function codes are not detected then the cursor codes are decoded at SET CURSOR FUNCTION to check for arrows, directional clicks or drag and those functions are sent to the host computer and return for a new scan at DO BASELINE SCAN.

With the microprocessor or processing means for the input device or control panel doing the aforementioned key interrogation or detection to decide if and what is being input the host that the input device or control panel is connected to is left completely free from using processing time for these functions, so with the host not doing any key scanning for key detection it can be made smaller and have no key scanning hardware or software.

Figure 15:
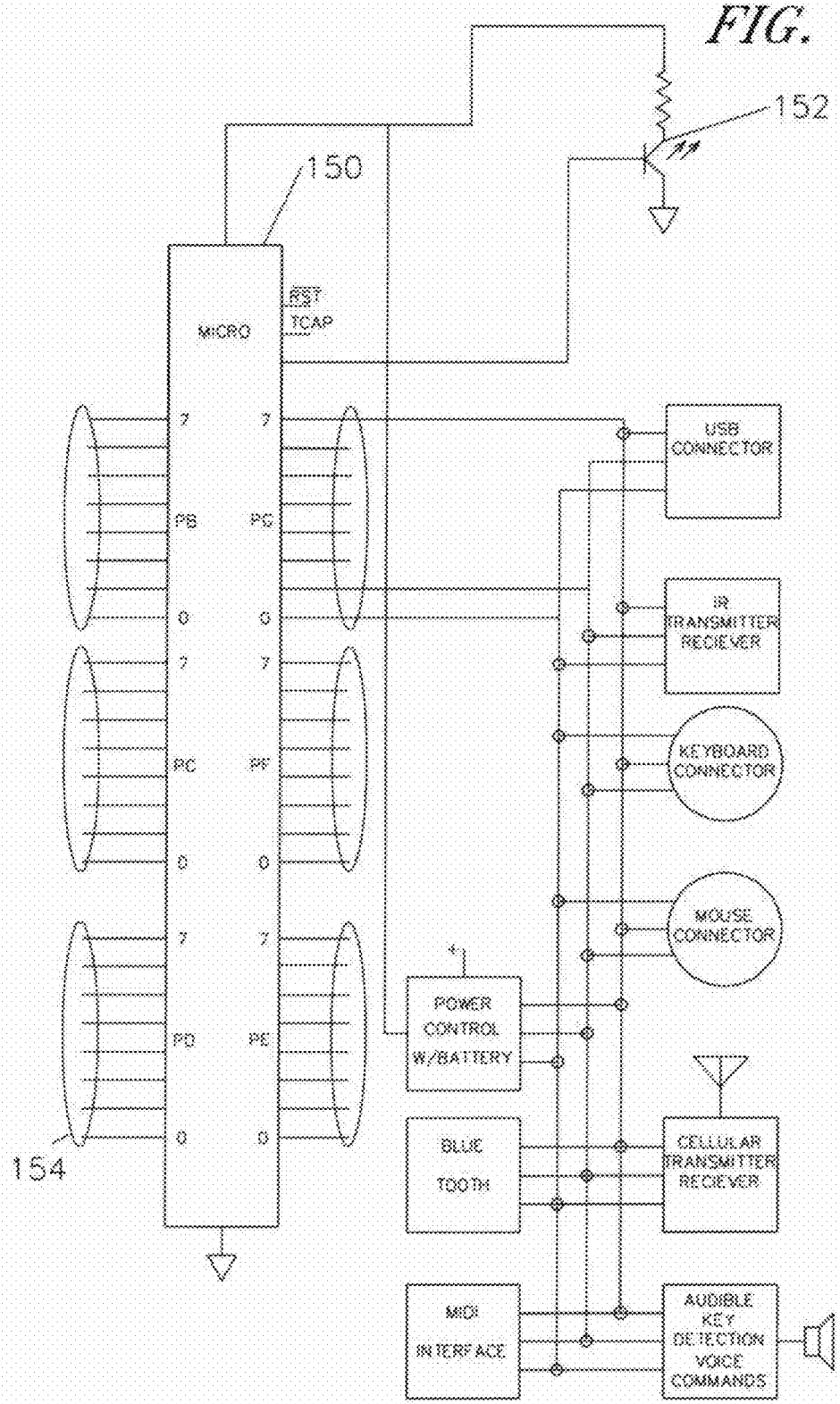
FIG. 15 is a schematic illustrating the microprocessor or processing means section of the input device in accordance with the teachings of this invention.

FIG. 15 is a schematic illustrating the microprocessor section of the input device with microprocessor 150 having ports for input, output, and analog as shown at 154. Light emitter 152 is for the caps lock function and illuminated when caps lock is set. The other input output blocks have their function shown in their corresponding blocks and those skilled in the art can appreciate more or less of these input outputs could also be used for communicating to a host computer. The POWER CONTROL block is for controlling the power to the input device where it can be a relay connected to a power source and when the relay is turned on and off so does the input device or parts thereof. When the POWER CONTROL is within the input device and microprocessor 150 is controlling the function then a small amount of power runs microprocessor 150 waiting for a on, off or partial control signal to perform the POWER CONTROL intended function, this signal could be but not limited to a RF interface from a hand held push button apparatus.

Figure 16:
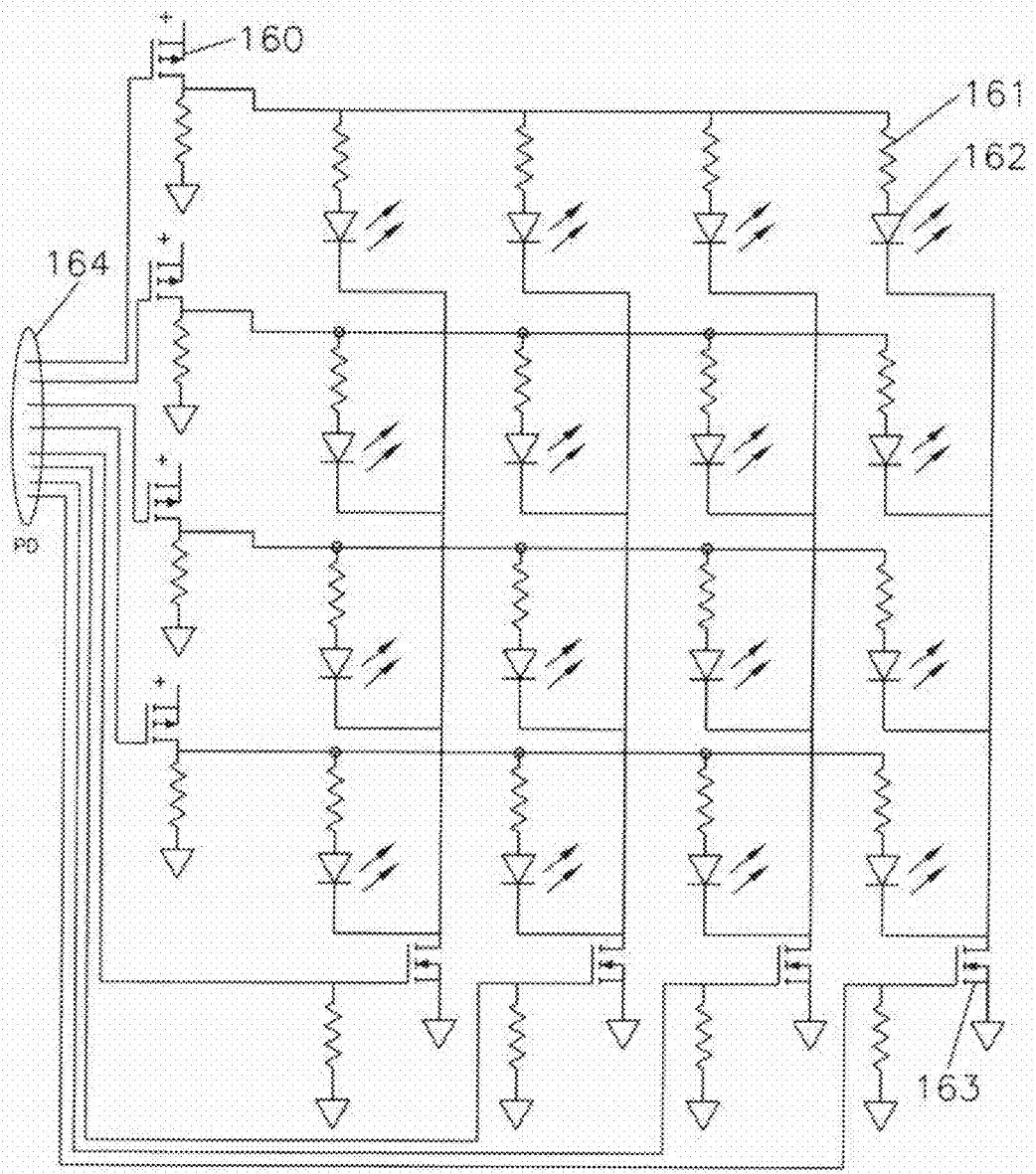
FIG. 16 is a schematic illustrating the light emitter output section of the input device in accordance with the teachings of this invention.

FIG. 16 is a schematic illustrating the LED output section of the input device or control panel with sixteen key positions showing a micro port interface 164 and FET 160 controlled through digital interface 164 biasing current limiting resistor 161 and output LED 162 to the positive allow LED 162 to be on when FET 163 controlled through digital interface 164 is biased to ground.

Ones skilled in the art can appreciate that all LED's in the shown matrix can be individually turned on and off by different control lines through digital interface 164, and that the matrix can be made larger or smaller depending on the application to facilitate more or less key position.

Figure 17:
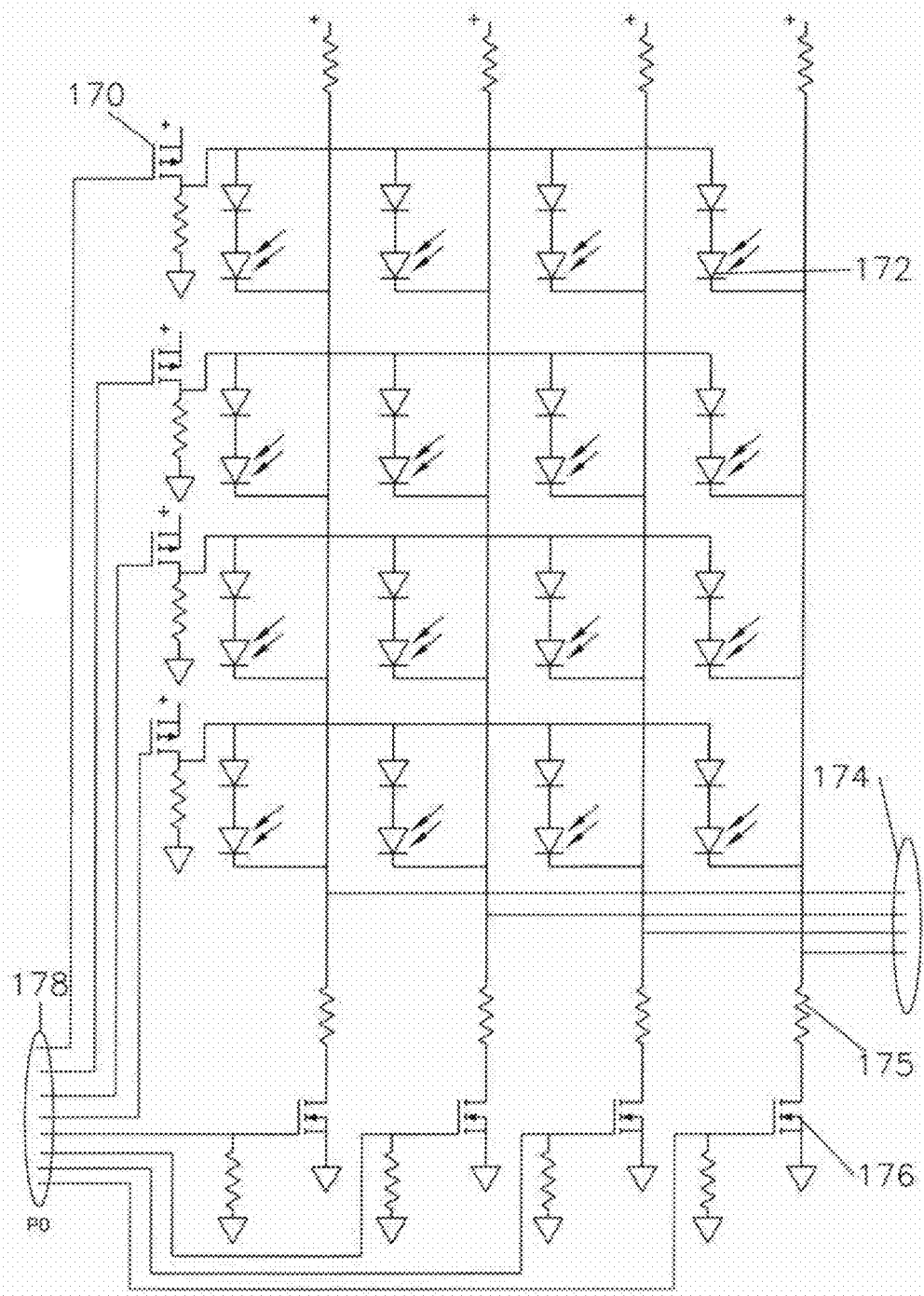
FIG. 17 is a schematic illustrating the light detector section of the input device in accordance with the teachings of this invention.

FIG. 17 is a schematic illustrating the photo sensor section of the input device with sixteen key positions showing a micro port digital interface 178 and FET 170 controlled through digital interface 178 biasing photo sensor 172 positive and turning photo sensor 172 on when FET 176 controlled by digital interface 178 showing a voltage over sense resistor 175 representative of the amount of light sensed by photo sensor 172 to be output to micro port analog interface 174. Ones skilled in the art can appreciate that all LED's in the shown matrix can be individually turned on and off by different control lines through interface 178 and analog interface port 174, and that the matrix can be made larger or smaller depending on the application to facilitate more or less key position.

It should be appreciated to those skilled in the art that input device and control panel are used to give a name directed as to how the invention is being used and should be realized that both names refer to the same basic invention being a peripheral to a computer and not an integral part of a computer, standalone being like a PC keyboard that is also called a desktop device which could be called other names, photo sensor and light beam detector being the same, and LED and light emitter being the same.

While the invention has been described in terms of a single preferred embodiment, those skilled in the art will recognize that the invention can be practiced with modification within the spirit and scope of the appended claims.

Having thus described my invention, what I claim as new and desire to secure by Letters Patent is as follows:

1. A light activated peripheral standalone input device to be used in and out of sunlight, comprising:
    a top cover with a plurality of semi-transparent locations with key indicia;
    said key indicia are fixed in location;
    said key indicia are associated with a key code;
    said key indicia are associated in location to each of said plurality of said semi-transparent locations;
    a plurality of light emitters and a plurality of light detectors arranged in a matrix associated in location to each of said plurality of said semi-transparent locations;
    said plurality of light detectors and said plurality of light emitters are disposed on a printed wiring board;
    said printed wiring board is aligned with a bottom cover;
    a processing means disposed on said printed wiring board with a program and associated circuitry to scan each of said plurality of light emitters and said plurality of light detectors;
    said processing means scans said plurality of light detectors and stores an ambient baseline reading of amplitude to be used for reference for detecting said light beam in sunlight or out of sunlight;
    wherein when a light beam is positioned over one of said plurality of light detectors said light beam is detected and said processing means communicates said key code to a host; and
    whereas all scanning resultant to obtain said key code is within said processing means.

2. A light activated peripheral standalone input device to be used in and out of sunlight as claimed in claim 1, further including
    a light source;
    said light source emits said light beam.

3. A light activated peripheral standalone input device to be used in and out of sunlight as claimed in claim 1,
    wherein said key code is delayed for a delay time from when said light beam is detected and said processing means outputs said key code to said host.

4. A light activated peripheral standalone input device to be used in and out of sunlight as claimed in claim 3,
    wherein an amount of time said delay time is adjustable from when said light beam is detected and said processing means outputs said key code to said host.

5. A light activated peripheral standalone input device to be used in and out of sunlight as claimed in claim 3,
    wherein if said light beam detection is interrupted during said delay time said processing means continues to scan other said detectors and no input of said key code to said host is output.

6. A light activated peripheral standalone input device to be used in and out of sunlight as claimed in claim 1,
    wherein said key indicia form at least a qwerty pattern of keys.

7. A light activated peripheral standalone input device to be used in and out of sunlight as claimed in claim 1,
    wherein said key indicia form at least a cursor control pattern of keys.

8. A light activated peripheral standalone input device to be used in and out of sunlight as claimed in claim 1, further including
    a plurality of finger detection emitters and finger detection detectors disposed around the periphery of said printed wiring board;
    said finger detection emitters and finger detection detectors forming a finger detection matrix; and
    wherein when a finger is placed in said finger detection matrix and an X and Y location within said matrix detecting said finger is aligned with a key indicia said key code for that said key indicia is communicated to said host by said processing means.

9. A light activated peripheral standalone input device to be used in and out of sunlight as claimed in claim 1
    wherein said key indicia is indicative of motorized wheelchair controls for at least speed of a wheelchair, direction of a wheelchair, and motion of a wheelchair.

10. A light activated peripheral standalone input device to be used in and out of sunlight as claimed in claim 1, further including
    a speaker for at least outputting an audible sound when said processing means detects said light beam.

11. A light activated peripheral standalone input device to be used in and out of sunlight as claimed in claim 1, wherein at least one of said light emitters is turned on as a response to said detector detecting a light beam.

12. A light activated peripheral standalone input device to be used in and out of sunlight as claimed in claim 1, further including
   means for automatic compensation for in said sunlight and out of said sunlight detection of said light beam;
   wherein the amplitude of said light beam is near the amplitude of said sunlight; and
   wherein said processing means separates said light beam from said sunlight using multi-sample summing digital signal processing.

13. A light activated peripheral standalone input device to be used in and out of sunlight as claimed in claim 10,
   wherein, said speaker outputs verbal commands.

14. A light activated peripheral standalone input device to be used in and out of sunlight as claimed in claim 1, further including
   a power control, and
   wherein said host can issue a command to turn on and off all or part of said power control.

15. A light activated peripheral standalone input device to be used in and out of sunlight as claimed in claim 1, further including
   a display; and
   wherein when said light beam is detected said processing means communicates said key code to said display, and a character representative of said key code is displayed on said display.

16. A light activated peripheral standalone input device to be used in and out of sunlight as claimed in claim 2, wherein said light source is turned on and off by said processing means and host via normal host to keyboard interchange commands.

17. A light activated peripheral standalone input device to be used in and out of sunlight as claimed in claim 2, further including
   a tilt switch means; and
   wherein when said light source is tilted said tilt switch means controls the on and off of said light beam.

18. A light activated peripheral standalone input device to be used in and out of sunlight as claimed in claim 2, further including
   a second light beam; and
   wherein said second light beam is visible light and said light beam is infrared light.

19. A light activated peripheral standalone input device to be used in and out of sunlight as claimed in claim 1, wherein said processing means periodically scans only a subset of said plurality of light detectors, and when changes from said ambient baseline are detected, said processing means scans said plurality of light detectors and stores a new ambient baseline reading of amplitude to be used for reference for detecting said light beam in sunlight or out of sunlight.

20. A light activated peripheral standalone input device to be used in and out of sunlight as claimed in claim 9, wherein said standalone input device is attached to a wheelchair.

\* \* \* \* \*